United States Patent [19]

Boyarsky et al.

[11] 4,393,869

[45] Jul. 19, 1983

[54] ELECTRONICALLY CONTROLLED RESPIRATOR

[75] Inventors: Abraham Boyarsky, Montreal; Jack Friedman, Cote St. Luc; Athanasios Christodoulopoulos, St. Laurent; Rock Lee, St. Hubert, all of Canada

[73] Assignee: Canadian Patents & Development Limited, Ottawa, Canada

[21] Appl. No.: 276,151

[22] Filed: Jun. 22, 1981

[51] Int. Cl.³ ............................................ A61M 16/00
[52] U.S. Cl. ........................ 128/204.18; 128/204.21; 128/204.23
[58] Field of Search ................. 128/204.18, 204.21, 128/203.23

[56] References Cited

U.S. PATENT DOCUMENTS 3,961,627 6/1976 Earnst et al. .................... 128/204.21

OTHER PUBLICATIONS

Jain et al., A Control System for Long Term Ventilation of the Lungs.

Primary Examiner—Richard J. Apley
Assistant Examiner—George Yanulis
Attorney, Agent, or Firm—Edward Rymek

[57] ABSTRACT

The breathing cycle of a patient is controlled to achieve proper ventilation and at the same time minimize the work of distension of the lungs. Oxygen enriched air is delivered to the patient during the inspiration period such that the pressure waveform is a ramp function having initial and final values which are dependent on the resistance, compliance and alveolar volume of the lungs. The apparatus includes a source of oxygen enriched air at a regulated pressure and a pneumatically controlled pressure reducing valve for reducing the pressure of the oxygen enriched air for delivery to the patient. The valve is controlled by a transducer which converts an electrical control signal into a pneumatic control signal. The electrical control signal which is generated by an electronic control circuit, is a function of the parameters of the patient's lungs.

8 Claims, 8 Drawing Figures

ELECTRONICALLY CONTROLLED RESPIRATOR

BACKGROUND OF THE INVENTION

This invention is directed to a method and an apparatus for artificially ventilating patients—especially young infants—and in particular, to a ventilation method which utilizes electronically predetermined pressure control for the minimization of work done on lung tissues.

The ideas proposed grew out of observation that newborn infants who require prolonged mechanical ventilation are subject to a variety of complications that increase in frequency with time on the respirator. Such conditions as pneumothorax (rupture of the lung), mediastinal emphysema (air in the mid-chest), circulatory compromise [J. H. Comroe, Physiology of Respiration, Year Book Med. Publ. Inc., Chicago, 1970, Sec. Ed.], bronchopulmonary dysplasia [W. H. Northway et al, Pulmonary disease following respirator therapy of hyaline membrane disease—bronchopulmonary dysplasia, N. Eng. J. Med. 276, 357, 1967], and oxygen toxicity [D. K. Edwards et al, Twelve years' experience with broncho pulmonary dysplasia, Ped. Vol. 59, 839–846, 1977], have all been related to the use of current mechanical ventilators.

Much research has gone into isolating the factors responsible for lung damage. Though there is controversy in this area, it seems to be generally accepted that high oxygen concentrations [B. E. Welch et al, Time concentration effects in relation to oxygen toxicity in man, Federation Proc. 22, 1053–1056, 1963] and high peak airway pressures [A. Taghizadeh et al, Pathogenesis of bronchopulmonary dysplasia following hyaline membrane disease, Am. J. Path. 82, 241–264, 1976] are linked to pathological outcomes. The difficulty in mitigating these factors has been the requirement to provide patients with adequate ventilation in the face of stiff compromised lungs.

The dilemma is particularly acute in the case of newborn infants with Respiratory Distress Syndrome (a condition of lung immaturity and deficiency of surfactant material) where prolonged respirator therapy may be required. The most dreaded long term complication, bronchopulmonary dysplasia (destructive fibroplastic changes in lung tissue), can result in fatality or chronic pulmonary insufficiency lasting months or years. Though the precise cause of this condition is not clear, a retrospective pathological study done by A. Taghizadeh (mentioned above) has implicated the use of high peak airway pressures. It is of interest that in clinical trials with infants [E. O. R. Reynolds et al, Improved prognosis of infants mechanically ventilated for hyaline membrane disease, Arch. Dis. Child. 49, 505, 1974], the lowering of peak airway pressures; slowing of respiratory frequencies and increasing of inspiratory to expiratory time ratios has resulted in improved survival largely by reducing the overall incidence of bronchopulmonary dysplasia. Other work [J. Stocks et al, The tole of artificial ventilation, oxygen and CPAP in the pathogenesis of lung damage in neonates: Assessment by serial measurements of lung function, Ped. Vo. 57, 352–362, 1976; and J. Stocks et al, Airway resistance in infants after various treatments for hyaline membrane disease: Special emphasis on prolonged high levels of inspired oxygen, Ped. 61, 178–183, 1978] has also implicated high pressure as a factor while the contribution of high oxygen concentration alone has been questioned [A. G. S. Philip, Oxygen plus pressure plus time: The etiology of broncho pulmonary dysplasia, Ped. Vol. 55, no. 1, Jan. 1975; and V. A. Pusey et al, Pulmonary fibroplasia following prolonged artificial ventilation of newborn infants, Can. Med. Assoc. 100, 451, 1969].

Though current research in this area has been focussing on the effects of various pressure wave forms on respiration [S. J. Boros, Variations in inspiratory:expiratory ratio and airway pressure wave form during mechanical ventilation: The significance of mean airway pressure, J. of Ped., Vol. 94, no. 1, 114–117, 1979], mechanical ventilators now in use are limited in providing either sinusoidal, square or triangular waves which must be manually set with regard to amplitude, frequency and duration. Though adequate blood gas values are the criteria used by the medical operator, there is currently no good way in which he can adjust for changing lung parameters such as resistance and compliance. Thus there is little control of the pressure damage or work done on the tissues being inflated.

A mathematical analysis of the data of Reynolds et al (mentioned above) comparing their modified wave form (low frequency, long inspiratory cycle, square wave) with others commonly in use (high frequency, short inspiration cycle, square or sinusoidal wave) suggests that the calculated quantity of work done is significantly less in the former despite comparable peak pressures.

Most respirator or ventilator systems which are presently used have been designed to deliver a preselected volume of gas to a patient. These are exemplified by U.S. Pat. No. 3,834,381, issued Sept. 19, 1974 to V. M. Peterson; U.S. Pat. No. 3,905,362, issued Sept. 16, 1975 to T. B. Eyrick et al; U.S. Pat. No. 3,985,131, issued Oct. 12, 1976 to K. E. Buck et al; and U.S. Pat. No. 4,036,221, issued July 19, 1977 to D. Hillsman et al. These devices though mainly concerned with the volume of gas delivered per inspiration/expiration cycle may also place limitations on other parameters in the gas delivery system. U.S. Pat. No. 3,905,362 places a preselected limit on the flow rate. U.S. Pat. No. 3,985,131 has a pair of different size volume chambers to provide a choice of ventilating modes. U.S. Pat. No. 4,036,221 includes a feedback circuit for assuring that the desired volume waveform is followed during each cycle.

Other respirators are pressure controlled, and usually interrupt gas flow when a predetermined pressure is reached at the patient. U.S. Pat. No. 3,961,627 monitors gas flow and pressure at the patient, these measurements are compared to values fixed by the doctor for adjustment of the control valve.

SUMMARY OF THE INVENTION

It is, therefore, an object of this invention to provide a method of ventilating a patient and a respirator which minimizes the work of distension on the alveoli tissue of the lung while it is being ventilated artificially.

In order to control the breathing cycle of a patient to achieve proper ventilation and at the same time minimize the work of distension of the lungs, the total resistance R and total compliance C of the patient's lung is determined, these totals will include the resistance and compliance of all airways leading from the mouth to the lungs. In addition, the alveolar tidal volume $V°_{AT}$ is also determined. Oxygen enriched air is then delivered to the patient for an inspiration period $\tau$ of the breathing cycle starting at an initial pressure $R\ V°_{AT}/\tau$ and increasing to a pressure $$\frac{R\ V_{AT}}{\tau} + \frac{V_{AT}}{C}$$

at the end of the inspiration cycle. After the inspiration period, the pressure is lowered to a level below $R\ V°_{AT}/\tau$ for a period of time to complete the breathing cycle. This pressure level may be at or slightly above atmospheric pressure. The volume of oxygen enriched air delivered to the patient may also be controlled and the inspiration and expiration periods may be selected to be within the standard norms.

The respirator system ventilates the patient's lungs following a breathing cycle having an inspiration period and an expiration period. The system includes a source of oxygen enriched air at a regulated pressure and a pneumatically controlled pressure reducing valve for reducing the pressure of the oxygen enriched air in accordance with a predetermined pressure waveform for delivery to the patient. The valve is controlled by a transducer which converts an electrical control signal into a pneumatic control signal. The electrical control signal is generated by an electronics control circuit, as a function of the parameters of the patient's lungs.

The system may also include a flow control valve to control the volume of oxygen enriched air delivered to the patient during the inspiration period, and a exhaust valve for exhausting the air from the patient during the expiration period.

The control signal is generated in the control circuit by a ramp generator. The ramp signal has an inspiration period $\tau$, and is given by the function $$\frac{RV°_{AT}}{\tau} + \frac{V°_{AT}t}{C}$$

where
  R is the total resistance,
  C is the total compliance,
  $V°_{AT}$ is the alveolar tidal volume, and
  t is the variable time, increasing from 0 to $\tau$.

In addition, the control circuit includes a timing circuit for controlling the duration of the inspiration period $\tau$ and the expiration period by generating a signal to control the exhaust valve.

Many other objects and aspects of the invention will be clear from the detailed description of the drawings.

DETAILED DESCRIPTION

Figure 1:
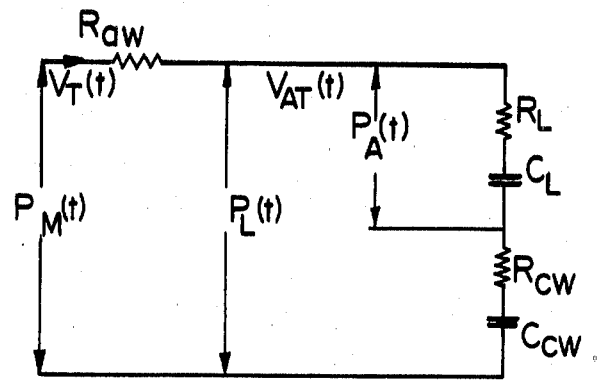
FIG. 1 is a model of the lungs based on their resistance and compliance.

The model for lung dynamics is illustrated in FIG. 1 wherein tissue compliance is symbolized as a capacitance and the resistance to airflow is symbolized as a resistance. It includes all resistance and compliances affecting airflow and, therefore, the term lung or lungs will include all airways from the mouth in addition to the lung organs themselves. The resistances $R_{aw}$, $R_L$ and $R_{cw}$ are the airway resistance, the lung (organ) resistance, and the chest wall resistance, respectively. $C_L$ and $C_{cw}$ are the lung compliance and chest wall compliance, respectively.

Both lung resistance and compliance vary from patient to patient depending on the age and size of the infant, as well as the extent of the diseased tissue in the lung. Also, they are not static values or completely linear functions and may vary in different areas of the lung and at different volumes. Nonetheless, these parameters are commonly employed and useful estimates of the function of an exceedingly complex mechanical structure. The different parameter values may presently be obtained from tables which are prepared from measurements taken on large numbers of infants. However, various methods are presently being development by which the actual compliance and resistance values of an infant's lungs may be measured.

In order to determine the ideal breathing pressure cycle which will minimize the work of distension alone by the lung tissue, it is necessary to study the pressure equations of the lungs with its relationship to the volumes involved.

Let $V_O$ denote the total alveolar volume when there is no pressure applied to the lung, and $V_{AT}(t)$ the change in alveolar volume as a function of time when pressure is applied, i.e., $V_{AT}(t)$ = alveolar volume at time $t - V_O$.

Let $\tau$ be the inspiration time. Then $V_{AT}(\tau) \equiv V°_{AT}$ is referred to as the alveolar tidal volume. The (total) tidal volume, $V_T$, consists of two parts: the volume that enters the dead space, $V_{DT}(t)$ and $V_{AT}(t)$. Thus $V_T(t) = V_{DT}(t) + V_{AT}(t)$. The air contributing to $V_{DT}(t)$ moves through air passes, meeting only the airway resistance $R_{aw}$, while $V_{AT}(t)$ represents the air that continues on into the lung, thereby encountering $R_L$, $R_{cw}$, $C_L$, $C_{cw}$ as well as $R_{aw}$. Let $P_M(t)$, $P_L(t)$, $P_A(t)$ denote, respectively, the pressures at the mouth, across the lung and chest wall, and across the alveolar tissue, all as functions of time. From FIG. 1, $$P_L(t) = \left(\frac{1}{C_L} + \frac{1}{C_{cw}}\right) V_{AT}(t) + (R_L + R_{cw})\dot{V}_{AT}(t) \quad (1)$$

and $$P_M(t) = R_{aw}\dot{V}_T(t) + P_L(t) \quad (2)$$

If the dead space fills up quickly, then it can be assumed that $\dot{V}_T(t) \simeq \dot{V}_{AT}(t)$ for all t except possibly for t close to the start of inspiration. Then, combining (1) and (2), $$P_M(t) = \left( \frac{1}{C_L} + \frac{1}{C_{cw}} \right) V_{AT}(t) + (R_{aw} + R_L + R_{cw}) \dot{V}_{AT}(t) \quad (3)$$

It is also noted that the pressure across the alveolar tissue is given by $$P_A(t) = \frac{V_{AT}(t)}{C_L} + R_L \dot{V}_{AT}(t) \quad (4)$$

The work of distension on the alveolar tissue is caused by the pressure $P_A(t)$. Since force x displacement is work, $P_A(t)[V_{AT}(t+\Delta t)-V(t)]$ denotes the work done on the alveolar tissue during the time duration $\Delta t$, from t to $t+\Delta t$. The total work done on the tissue during a breath is:

$$W(P_A) = \int_O^T P_A(t) \dot{V}_{AT}(t) dt, \quad (5)$$

where T is the total time duration of a breath and $W(P_A)$ denotes the dependence of work on the pressure waveform across the tissue, $P_A(t)$.

During inspiration, the pressure due to the respirator is doing work on the tissue. During expiration, the elastic property of the lung causes air to be pushed out, creating work on the respirator. We note that $\dot{V}_{AT}(t)$ is negative on the expiration phase of the breath, thereby making a negative contribution to $W(P_A)$. Since the lung is not perfectly elastic, the work done on the tissue will not be the same as the work done by the tissue. The difference is work that has been left in the tissue in the form of energy and heat. Heat causes a deterioration in the molecular structure of the material. The more energy left in the tissue, the more damage can be expected.

It is reasonable to assume that no matter what the inspiration pressure waveform is, once the alveolar tidal volume, $V°_{AT}$, has been attained, the expiration pattern will be the same. Hence, the energy left in the tissue depends only on the work done on the tissue during the inspiration phase of a breath. Therefore, only $W_I(P_A)$ need be of concern where $$W_I(P_A) = \int_O^\tau P_A(t) \dot{V}_{AT}(t) dt, \quad (6)$$

where $\tau$ is the inspiration time and $W_I(P_A)$ denotes the work done on the tissue during the inspiration phase of a breath.

In order to minimize the work on the alveolar tissue during inspiration, the optimal pressure waveform $P_M(t)$ at the mouth must be found given a desired alveolar tidal volume $V°_{AT}$. Using Euler's equation, a necessary condition for $W_I(P_A)$ to be minimized is that:

$$\frac{\partial F}{\partial V_{AT}} - \frac{d}{dt}\left( \frac{\partial F}{\partial \dot{V}_{AT}} \right) = 0 \quad (7)$$

where $$F = F(t, V_{AT}, \dot{V}_{AT}) = P_A(t)\dot{V}_{AT} +$$

$$\left( R_L \dot{V}_{AT} + \frac{V_{AT}}{C_L} \right) \dot{V}_{AT}, \text{ and } \frac{\partial F}{\partial Z}$$

denotes the partial derivative of F with respect to Z. Thus, on substituting for F into (7):

$$\frac{\dot{V}_{AT}}{C_L} - \frac{d}{dt}\left( R_L \dot{V}_{AT} + \frac{V_{AT}}{C_L} + R_L \dot{V}_{AT} \right) = 0,$$

resulting in:

$$-2R_L \ddot{V}_{AT} = 0$$

or $$\ddot{V}_{AT} = 0 \quad (8)$$

Integrating twice:

$$V_{AT}(t) = K_1 t + K_2, \quad (9)$$

where $K_1$ and $K_2$ are constants. Noting that at $t=0$ (the beginning of inspiration), $V_{AT}(0)=0$, then $K_2=0$. At the end of inspiration, $V_{AT}(t)$ is equal to the alveolar tidal volume $V°_{AT}$: $V_{AT}(\tau) = V°_{AT}$. Using this in (9) yields:

$$V°_{AT} = K_1 \tau.$$

Thus, $K_1 = V°_{AT}/\tau$, and equation (9) becomes $$V^*_{AT}(t) = \frac{V°_{AT} t}{\tau} \quad (10)$$

where $V^*_{AT}(t)$ denotes the optimal alveolar tidal volume dynamics.

On substituting (10) into (3):

$$P^*_M(t) = \frac{V°_{AT}}{C_T} t + \frac{R V°_{AT}}{\tau} \quad (11)$$

where * denotes the optimal value, $R = R_{aw} + R_L + R_{cw}$ and $$\frac{1}{C} = \frac{1}{C_L} + \frac{1}{C_{cw}}$$

Figure 2:
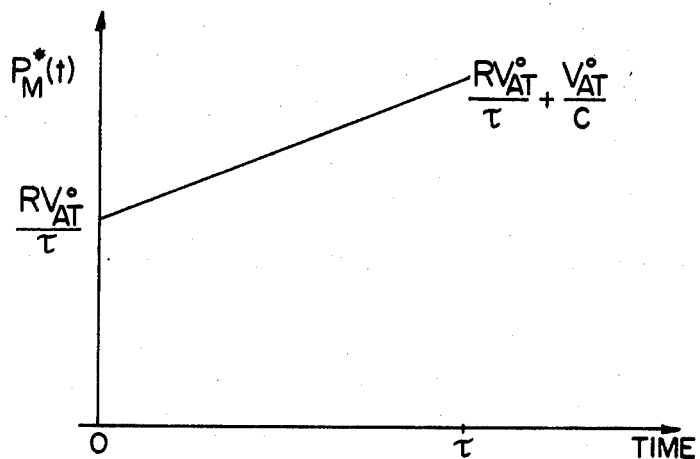
FIG. 2 illustrates the optimal pressure waveform at the mouth for inspiration.

A typical optimal pressure waveform at the mouth is shown in FIG. 2. At the outset of inspiration, the pressure rises quickly to $RV°_{AT}/\tau$ and then it increases until the alveolar tidal volume is attained at the level $$\frac{R V°_{AT}}{\tau} + \frac{V°_{AT}}{C}$$

after a time $\tau$. After time $\tau$, the pressure drops down abruptly. This pattern includes an abrupt application of pressure initially at a time when the volume of the alveoli is small, since this initial pressure will not cause significant stretching. However, as the volume increases and stress becomes significant, the pressure is increased gently and gradually, until the alveolar tidal volume is attained, ensuring adequate ventilation. Such a pressure waveform minimizes the work of inspiration on the alveolar tissue. The pressure is shown to increase linearly in accordance with equation (11), however, this linearity may be compromised somewhat early in the cycle due to the mechanisms of the respirator. It is further to be noted from equation (11) that the initial and final pressure levels of the inspiration cycle are inversely proportional to the length of the inspiration cycle $\tau$.

An HMD patient, for example, may have the following case data.

$R_{aw} = 0.10$ cm $H_2O$/ml/sec
$C_L = 2.0$ ml/cm $H_2O$
$C_{cw} = 2.0$ ml/cm $H_2O$
$V_T = 22$ ml
$V_{DT} = 9$ ml
Breathing cycle = 1 sec The alveolar tidal volume $V°_{AT}$ is $V_T - V_{DT} = 22 - 9 = 13$ ml. $R_L$ and $R_{cw}$ are known each to be 0.20 the total resistance R and $$\therefore R = (R_{aw} + R_L + R_{cw})$$

$$R = 0.10 + 0.2R + 0.2R$$

$$\therefore R = 0.166 \text{ cm } H_2O/\text{ml/sec}.$$

Substituting this data in equation (11), $$P^*(t) = \frac{13}{\tau} t + \frac{2.16}{\tau}$$

In this solution, the inspiration time is not yet selected, though it may be set at approximately half of the total cycle of 1 sec. It is known from studies, however, that the optimal mean airway pressure (MAP) is between 11 and 14 cm $H_2O$. Taking the optimal pressure equation and integrating for MAP:

$$MAP = \frac{1}{\tau} \int_O^\tau \left( \frac{13}{\tau} t + \frac{2.16}{\tau} \right) dt$$

$$(MAP)\tau = \frac{13}{2} \tau + 2.16, \tau = \frac{2.16}{(MAP) - 6.5}$$

For the above lung parameters, the range of the inspiration time and pressure parameters are shown in Table 1 below.

TABLE 1

| MAP (cm H2O) | $\tau$ (sec) | $P_M(O)$ (cm H2O) | $P_M(\tau)$ (cm H2O) |
|---|---|---|---|
| 11 | 0.48 | 4.5 | 17.5 |
| 14 | 0.29 | 7.4 | 20.4 |

Figure 3:
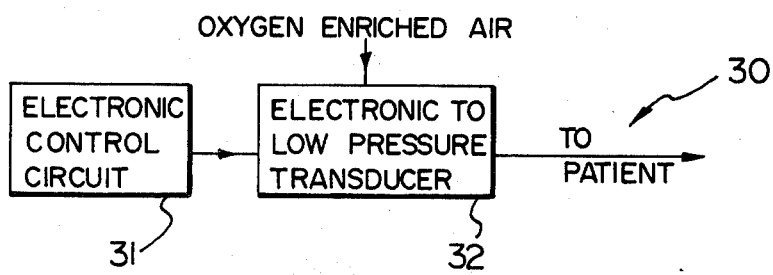
FIG. 3 illustrates the basic components of the respirator in accordance with the present invention.

The respirator 30, in accordance with the present invention, includes two main components, as illustrated in FIG. 3, the electronic control 31 with a pressure waveform generator as its main element, and the electronic-to-low-pressure transducer 32. The electronic control 31 provides the waveform signal for controlling the respiration cycle and the gas pressure to the patient. The electronic-to-low-pressure transducer 32 uses the waveform signal to actually control the flow of oxygen enriched air to the patient.

Figure 4:
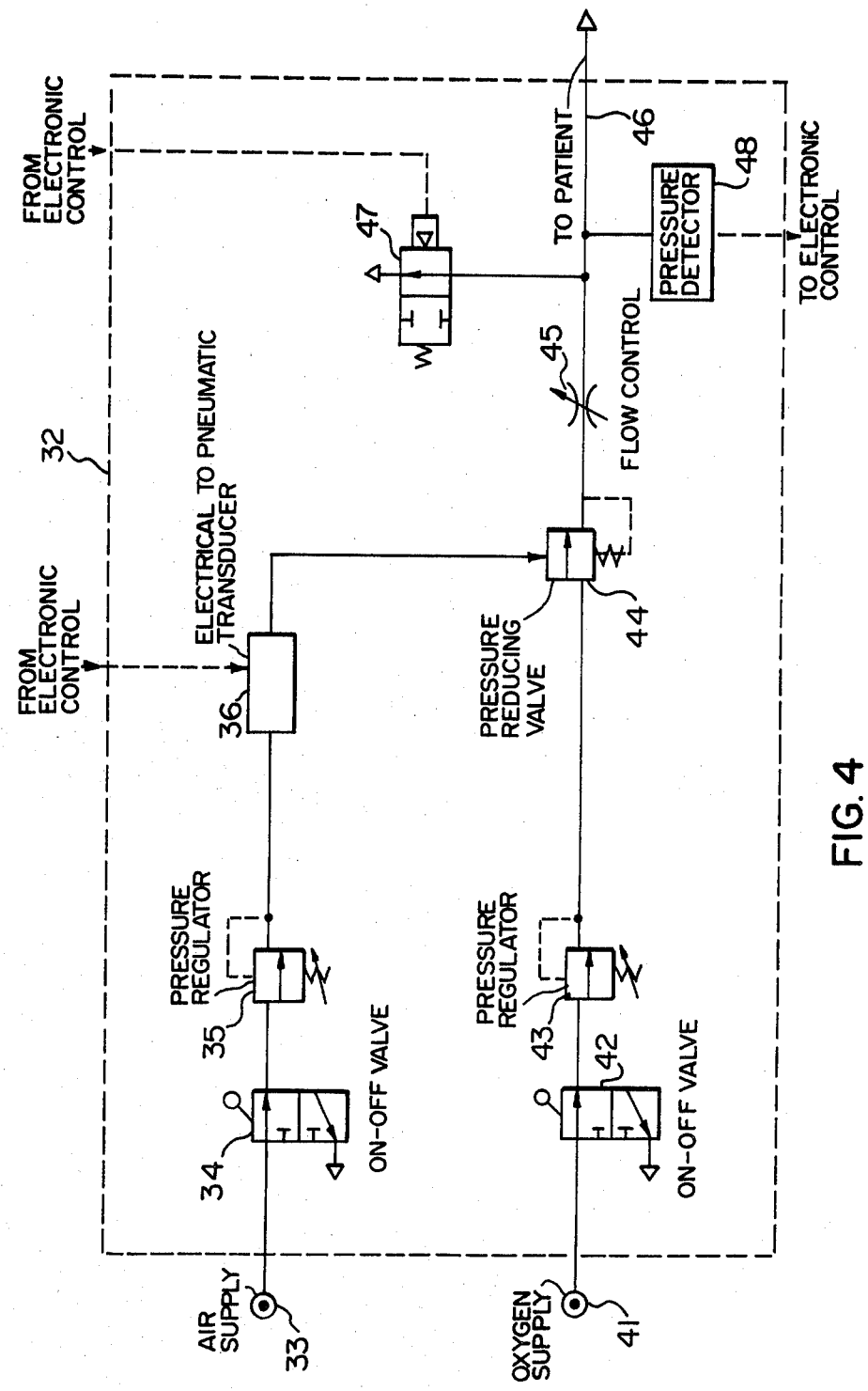
FIG. 4 is a schematic of the pneumatic component of the respirator.

A schematic of the transducer 32 is shown in FIG. 4. A first pneumatic circuit for developing a pneumatic control signal includes an air supply 33, a standard on-off valve 34 for opening or closing the air supply 33, a regulator 35 for regulating the pressure of the air supply to some fixed value and an electrical-to-pneumatic transducer 36 for controlling the pressure of the regulated air in accordance with a predetermined electrical signal to form the pneumatic pressure control signal. The electrical signal is received from the control 31. The electrical-to-pneumatic transducer 36 may be any one of a number available such as the Fairchild Model T5100 Series Transducer or the Moore Series 77 E/P transducer. These transducers convert an electrical signal in a ma range into a pneumatic signal in a 3–15 psi range.

Figure 5:
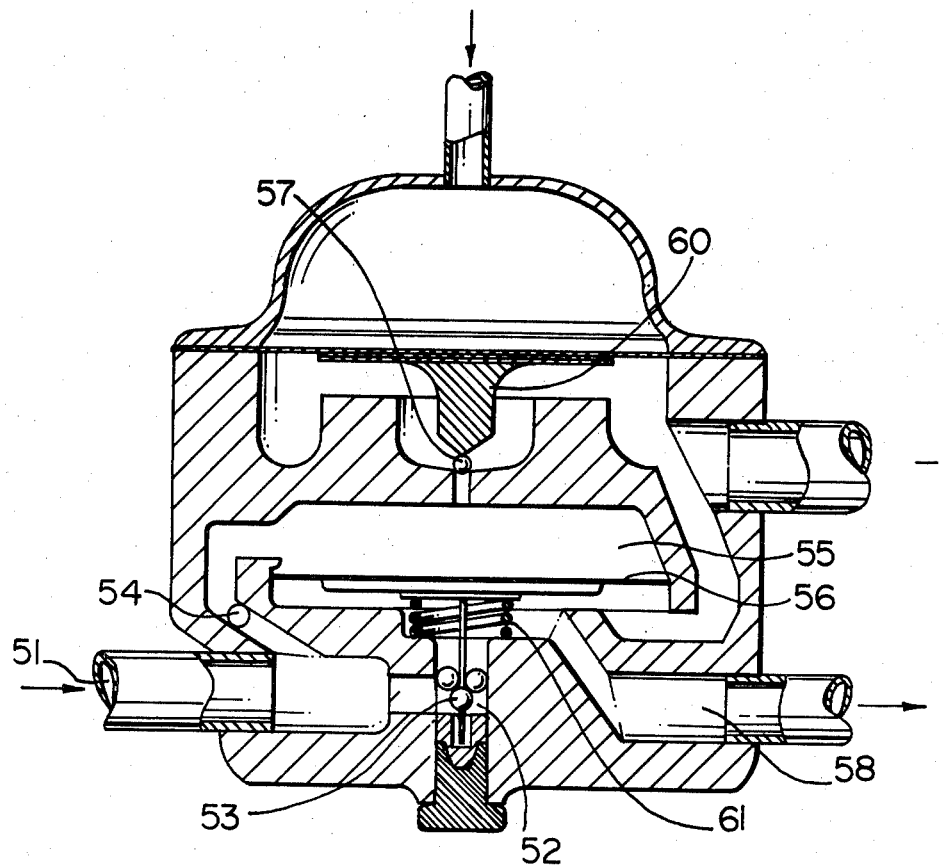
FIG. 5 in cross-section, illustrates a pneumatic controlled pressure reducing valve.

The signal from the electrical-to-pneumatic transducer 36 is used to control the output of a pressure reducing valve in the second pneumatic circuit found in transducer 32. The second pneumatic circuit includes an oxygen enriched air supply 41 in which the oxygen component can be adjusted to any desired level. An on-off valve 42 opens or closes the supply and a regulator 43 regulates the pressure of the oxygen enriched air. The oxygen enriched is fed through a controlled pressure reducing valve 44 under the control of the pneumatic signal from transducer 36. Valve 44 allows the oxygen enriched air to pass through at a pressure in the range of 0–1 psi in response to the pneumatic signal from transducer 36. The valve 44 may be a modified Moore Model 40 Nullmatic Pressure Regulator as shown in FIG. 5, in which the valve stem and range spring are replaced by the pneumatic pressure signal from transducer 36.

The high pressure oxygen enriched air is fed into the valve through inlet 51. It may pass through to a supply port 52, under the control of a valve plunger 53. When plunger 53 is up and blocking the supply port 52, the air flows through a restriction screw 54, which is simply a needle valve controlling the air flow and eliminating the surge effects of a sudden increased admission of air. Past this screw 54, air enters the pilot pressure chamber 55 and starts to accumulate there against the exhaust diaphragm assembly 56. As the air accumulates, pressure builds up. If this pressure were sufficiently large it would activate the exhaust diaphragm 56 and the plunger 53 would descend. To control the pressure in chamber 55, air is allowed to escape through a nozzle 57 under the control of diaphragm assembly 60, where the air then follows a path down the right side of the valve and exits as the (reduced) regulated output to the patient. Normally, this air bleed-off is very small.

The valve is activated by the input pressure signal in the input chamber 50 on the upper diaphragm assembly 60. The force of the output pressure (3–15 psi) of the transducer 36 on diaphragm assembly 60, causes it to descend blocking off the nozzle 57. With no outlet, air pressure builds up in the pilot pressure chamber 55. This force opposes the spring 61 force and at some point, depending on the adjusted tension of the spring 61, overcomes the spring force, causing the valve plunger 53 to descend and the valve 53 controlling the supply port 52 to open. This allows air to flow through to the regulated output line 58.

When the input signal in chamber 59 stops, the valve plunger 53 rises again and the flow of supply air is cut off. If there is some disturbance in the breathing sequence, the pressure change is fed back along the regulated output line, forcing the plunger up or down, depending on the type of disturbance. With newborn infants there are usually no disturbances (cough, sneeze, etc.) and the regulated pressure output is controlled entirely by the signal in chamber 59.

The pressure attained in the pilot pressure chamber 55 depends on the spring 61 force; the higher the force, the higher the air pressure regulated to overcome it. When enough air escapes so that the pressure of the remaining air again equals the spring force x diaphragm area, the valve plunger 53 rises.

The pressure exerted by the pressure signal in chamber 59 serves to open or close the nozzle 57, while the exhaust diaphragm 55 is a balanced system with the opposing forces being the stored pressure and the pressure in the pilot pressure chamber 55. The oxygen enriched air pressure in outlet 58 is, therefore, directly related to the pressure signal in chamber 59.

Further, with reference to FIG. 4, the controlled pressure oxygen enriched air is fed through flow control valve 45 to the output line 46 and the patient. The flow control valve adjusts the flow rate of oxygen enriched air directed to the patient. This valve may be controlled manually or electronically by the electronic control 31.

After the inspiration portion of the cycle is completed, and valve 44 discontinues air flow, an exhaust valve 47 is opened to release line pressure until the beginning of the next breathing cycle. Exhaust valve 47 is also controlled by the electronic control 31.

A pressure detector 48 may also be connected into the output line 46 to provide line pressure signals to the electronic control 31, as means of maintaining a residual pressure in the lungs by closing valve 47 before the pressure returns to zero. Also, the signals from detector 48 to electronic control 31 are monitored to provide the actual duration of inspiration and expiration time lengths.

Figure 6:
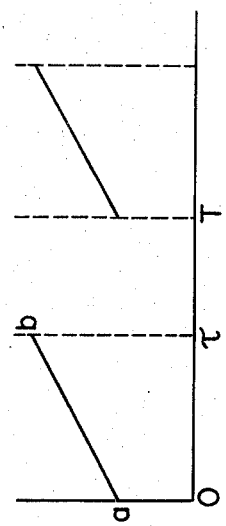
FIG. 6 illustrates the ramp signal for controlling the respirator.

From equation (11), the optimal pressure waveform is shaped as shown in FIG. 6, where $\tau$ is the inspiration time, T is the time of a breath, and a and b are the initial and final heights of the ramp. The electronic control circuit 31 should, therefore, be capable of varying these four parameters: a, b, $\tau$, T, over wide ranges, allowing for large variance in lung characteristics.

Figure 7:
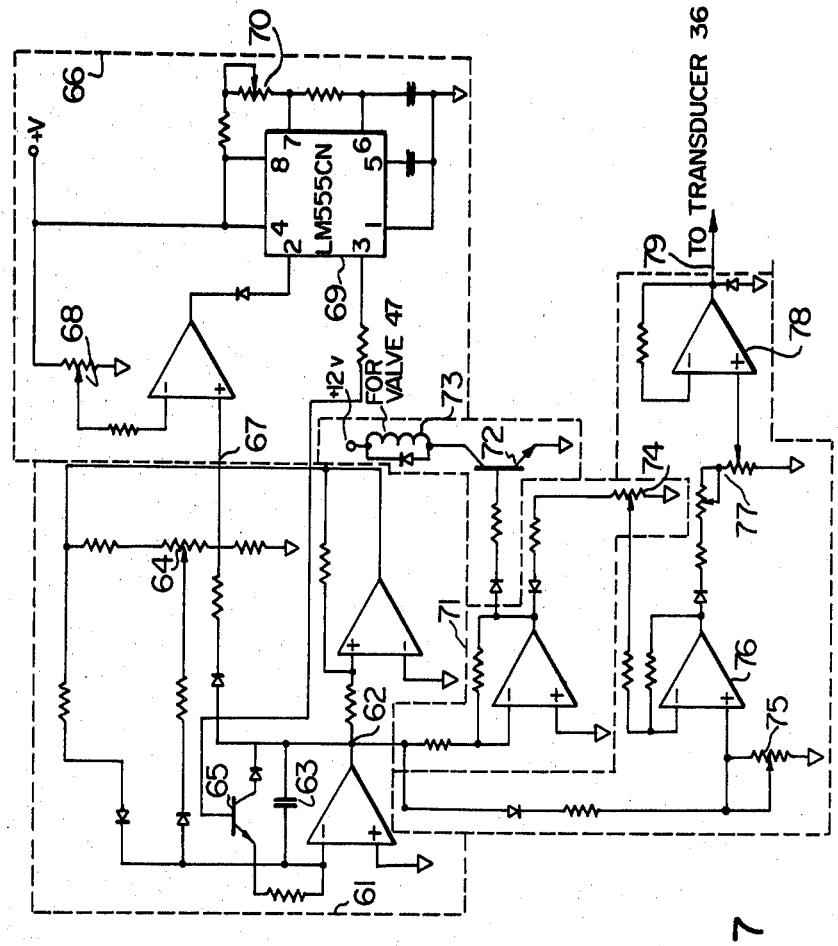
FIG. 7 illustrates an electronic control circuit for the respirator.

One embodiment of the electronic control circuit 31 is shown in FIG. 7. The control circuit includes a ramp generator 61 which produces a ramp function at its output 62. The slope of the ramp function is dependent on the potentiometer 64. The ramp function is initiated when transistor 65 is rendered non-conductive by the respiration cycle timing circuit 66. Once the ramp function at the input 67 reaches a value determined by potentiometer 68, bistable 69 causes transistor 65 to conduct. Transistor 65 remains on for a period of time determined by potentiometer 70.

The output of ramp generator 61 at 62 is a positive going ramp with a negative swing and is also applied to a high gain inverting amplifier 71 which drives the Darlington transistor 72 by the positive signal applied to it. A current is thus caused to flow through solenoid 73, which opens the exhaust valve 47 (FIG. 4) at the end of the inspiration cycle.

The positive portion of the output of ramp generator 61 is applied to the positive terminal of an amplifier 76 at a preselected level above ground determined by potentiometer 75. At the same time, the negative portion of the inverted output of ramp generator 61 is applied to the inverting terminal of amplifier 76 through a potentiometer 74. The output from inverter 76 will be a ramp function in which the initial height—a in FIG. 6—is determined by potentiometer 75. The remaining potentiometer 77 adjusts the total height of the ramp and amplifier 78 is a non-inverting current amplifier which can supply currents up to 200 milliamperes at output 79 for application to transducer 36 (FIG. 4).

Figure 8:
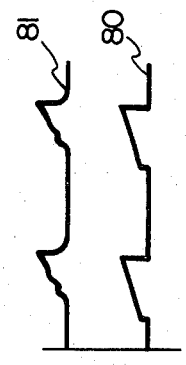
FIG. 8 illustrates the output of the control circuit and the pressure waveform of the oxygen enriched air produced by the respirator.

In FIG. 8, signal 80 is the ramp signal generated by the electronic control circuit at output 79 (FIG. 7) while signal 81 is the pressure waveform of the oxygen-enriched air at the output of the respirator as detected by detector 48 (FIG. 4). The slight oscillation at the outset of the pressure waveform is due to the dynamics of the pneumatic elements in the apparatus. The time delay between the signals is due to the travel time down the tubing to the patient. It is fairly constant over a large range of signals and hence can be compensated for in the electronic waveform to give the desired output pressure waveform.

Many modifications in the above described embodiments of the invention can be carried out without departing from the scope thereof and, therefore, the scope of the present invention is intended to be limited only by the appended claims.

We claim:

1. A method of controlling the breathing cycle of a patient comprising:
   determining the total resistance R of the patient's lungs;
   determining the total compliance C of the patient's lungs;
   determining the alveolar tidal volume $V°_{AT}$ of the patient's lungs;
   delivering oxygen enriched air to the patient for an inspiration period $\tau$ of the breathing cycle at an initial pressure $RV°_{AT}/\tau$ and increasing the pressure to a pressure $$\frac{R V°_{AT}}{\tau} + \frac{V°_{AT}}{C}$$

at the end of the inspiration cycle; and
   lowering the pressure to a level below $RV°_{AT}/\tau$ during an expiration period of the breathing cycle.

2. A method as claimed in claim 1 which includes the step of controlling the volume of oxygen enriched air delivered to the patient.

3. A method as claimed in claim 1 or 2 in which the inspiration period is approximately half of the breathing cycle.

4. A respirator system for ventilating the lungs of a patient in accordance with a breathing cycle having an inspiration period and an expiration period comprising:
   means for providing oxygen enriched air at a regulated pressure;
   pneumatically controlled pressure reducing valve for reducing the pressure of the oxyen enriched air in accordance with a predetermined pressure waveform for delivery to the patient;
   transducer means for converting an electrical control signal to a pneumatic control signal to control the pressure reducing valve; and
   electronic control circuit for generating the electrical control signal as a function of parameters of the lungs.

5. A respirator as claimed in claim 4 which further includes means for controlling the volume of oxygen enriched air delivered to the patient during the inspiration period.

6. A respirator as claimed in claim 4 which further includes valve means for exhausting the air from the patient during the expiration period.

7. A respirator as claimed in claim 4 wherein the electronic control circuit includes a ramp generator for generating a ramp control signal of period $\tau$, the ramp signal being a function of $$\frac{RV^\circ_{AT}}{\tau} + \frac{V^\circ_{AT}}{C\tau} t$$

where
- R is the total resistance,
- C is the total compliance,
- $V^\circ_{AT}$ is the alveolar tidal volume,
- $\tau$ is the inspiration period, and
- t is the instantaneous time in the period 0 to $\tau$.

8. A respirator as claimed in claim 7 wherein the electronic control circuit further includes means for controlling the inspiration period $\tau$ and means for generating a signal to control the exhaust valve means to open during the expiration cycle.

* * * * *